(12) United States Patent
Bellini et al.

(10) Patent No.: US 6,214,537 B1
(45) Date of Patent: *Apr. 10, 2001

(54) SYNTHETIC PEPTIDES AND MIXTURES THEREOF FOR DETECTING HIV ANTIBODIES

(75) Inventors: Francesco Bellini, Ville Mont-Royal; Gervais Dionne, St-Laurent; Martial Lacroix, Brossard, all of (CA)

(73) Assignee: Biochem Immunosystems, Inc., Quebec (CA)

(*) Notice: Subject to any disclaimer, the term of this patent is extended or adjusted under 35 U.S.C. 154(b) by 0 days.

This patent is subject to a terminal disclaimer.

(21) Appl. No.: 07/281,205

(22) Filed: Dec. 8, 1988

Related U.S. Application Data

(63) Continuation-in-part of application No. 07/185,518, filed on Apr. 22, 1988, now abandoned, which is a continuation-in-part of application No. 07/148,821, filed on Jan. 27, 1988.

(51) Int. Cl.$^7$ ..................................................... C12Q 1/70
(52) U.S. Cl. ................................ 435/5; 530/317; 530/324
(58) Field of Search ........................ 514/13, 12; 530/326, 530/325, 324, 327, 328, 317; 435/7, 5

(56) References Cited

U.S. PATENT DOCUMENTS

| | | | |
|---|---|---|---|
| 4,629,783 | * 12/1986 | Cosand | 530/324 |
| 4,735,896 | 4/1988 | Wang | 435/5 |
| 4,772,547 | 9/1988 | Heimer | 435/5 |
| 4,812,556 | * 3/1989 | Vahlne et al. | 530/324 |
| 4,879,212 | 11/1989 | Wang | 435/5 |
| 4,957,737 | * 9/1990 | Heimer et al. | 424/88 |

FOREIGN PATENT DOCUMENTS

| | | |
|---|---|---|
| 0219106 | 4/1987 | (EP) . |
| 0231914 | 8/1987 | (EP) . |
| 0233045 | 8/1987 | (EP) . |
| 0247557 | 12/1987 | (EP) . |
| 8606414 | 11/1986 | (WO) . |
| 8706005 | 10/1987 | (WO) . |
| 8903844 | 5/1989 | (WO) . |

OTHER PUBLICATIONS

Gnann, J. W., Science, 237: 1346–1349, Sep. 11, 1987.*
Gnann, J. W., The Journal of Infectious Diseases, 156 (2): 261–267, Aug. 1987.*
Bolz *J Virol Meth* 22, 173, 1988.*
Ratner et al., "Complete nucleotide sequence of the AIDS virus, HTLV–III", *Nature*, 313, pp. 277–284 (Jan. 24, 1985).
Alizon et al., "Genetic Variability of the AIDS Virus: Nucleotide Sequence Analysis of Two Isolates from African Patients", *Cell*, 46, pp. 63–74 (Jul. 4, 1986).
Wang et al., "Detection of antibodies to human T–lymphotropic virus type III by using a synthetic peptide of 21 amino acid residues corresponding to a highly antigenic segment of gp41 envelope protein", *Proc. Natl. Acad. Sci. U.S.A.*, 83, pp. 6159–6163 (Aug. 1986).
Gallaher, "Detection of a Fusion Peptide Sequence in the Transmembrane Protein of Human Immunodeficiency Virus", *Cell 50*, pp. 327–328, (Jul. 31, 1987).
Gnann et al., "Fine Mapping of an Immunodominant Domain in the Transmembrane Glycoprotein of Human Immunodeficiency Virus", *Jol. of Vir.*, 61(8), pp. 2639–2641 (Aug. 1987).
Bretscher, *Febs Letters 85*, 145, 1978.*
Ehrenberg, *Acta Chem Scand 43*, 177, 1989.*
Janolino, *Archiv Biochem Biophys 258*, 265, 1987.*
Hodges, *J. Biol. Chem. 256*, 1214, 1981.*
Cann, *Archiv Biochem Biophys 221*, 57, 1983.*
Paynovich, *Int. J. Pept. Prot. Res. 13*, 113, 1979.*
Seiber, *Helv Chim Acta 59*, 1489, 1976.*
Sisido, *Biopolymers 16*,2723, 1977.*
Gross, *The Peptides 3*, 146 and 161–162, 1981.*

* cited by examiner

Primary Examiner—Robert D. Budens
(74) Attorney, Agent, or Firm—Nixon & Vanderhye

(57) ABSTRACT

There is provided cyclic peptides of the general formula

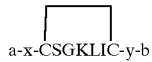
a-x-CSGKLIC-y-b wherein x represents the amino terminus, one amino acid or amino acid sequence starting with amino add 604 and going back as far as amino acid 586 (gp41-HIV-1); and y represents the carboxy terminus, an amino acid or amino acid sequence starting with amino acid 612 and extending up to amino acid 629 (gp41-HIV-1). There is also provided peptides of the general formula

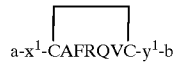
a-x$^1$-CAFRQVC-y$^1$-b wherein x$^1$ represents the amino terminus, one amino acid or amino acid sequence starting with amino add 596 and going back as far as amino acid 578 (gp42-HIV-2) and a and b represent the amino and carboxy terminals, respectively, as well as substituents which are effective to make the peptides more useful as an immunodiagnostic reagent; and y$^1$ represents the carboxy terminus, an amino acid or amino add sequence starting with amino acid 604 and extending up to amino acid 613 (gp42-HIV-2) and a and b are as defined previously. These cyclic peptides alone or in admixture with certain linear peptides are particularly useful in detecting HIV-1 and HIV-2 antibodies.

2 Claims, No Drawings

SYNTHETIC PEPTIDES AND MIXTURES THEREOF FOR DETECTING HIV ANTIBODIES

This is a continuation-in-part of U.S. patent applications Ser. No. 148,821 filed on Jan. 27, 1988, and Ser. No. 185,518 filed Apr. 22, 1988, now abandoned Bellini et al., inventors.

FIELD OF THE INVENTION

The present invention relates to novel cyclic synthetic peptides and combinations thereof with linear synthetic peptides for detecting HIV antibodies.

BACKGROUND OF THE INVENTION

It has been postulated that Acquired Immune Deficiency Syndrome (AIDS), AIDS related complex (ARC) and pre-AIDS are caused by a retrovirus, the Human Immunodeficiency virus type 1 HIV-1; also known as HTLV-III, LAV-1 and ARV). Recently another pathogenic human retrovirus named HIV-2 (formerly LAV-2) was isolated from west African patients with AIDS (Montagnier et al, in PCT/FR 87/00025, published on Jul. 30, 1987 under International Publication no. WO 87/04459). It has recently been shown (Guyader et al. Nature 326, 662–669, 1987) that HIV-2 shares a number of conserved sequences with HIV-1 and the Simian Immunodeficiency viruses (SIV).

Even though other numbering systems are used in the prior art referred to herein, the numbering systems for amino acids used herein is that of Ratner et al., Nature, 313 277–284, 1985 for the HIV-1 proteins and that of Guyader et al, Nature, 326, 662–669 (1987) for the HIV-2 proteins. The amino adds used herein in the peptides are given with the single letter code as follows: ala=A, arg=R, asn=N, asp=D, cys=C, gln=Q, glu=E, gly=G, his=H, ile=I, leu=L, lys=K, met=M, phe=F, pro=P, ser=S, thr=T, trp=W, tyr=Y and val=V.

The initial immunodiagnostic tests for the detection of antibodies in the serum of patients infected with HIV-1 utilized the whole virus as antigen. Second generation tests made use of polypeptide sequences obtained by the recombinant DNA methodology. Cabradilla et al. Bio/Technology 4 128–133 (1985) and Chang et al. Bio/Technology 3, 905–909 (1985) succeeded in obtaining bacterially synthesized viral protein fragments of 82 and 102 amino acid residues respectively. E.P. 86202314 and 86114243 describe recombinant polypeptides covering regions of the gp41 and gp120 that are immunoreactive alone or in mixtures. Shoeman et al. Anal. biochem. 161, 370–379 (1987) also describe several polypeptides from gp41 that have immunoreactive properties with antibodies present in sera from patients infected with HIV-1. None of the above assay procedures is acceptable. Their lack of sensitivity is serious as it may permit blood containing virus to escape detection and thereby potentially res the infect blood product receivers. The impurities present in these antigen preparations are also responsible for unacceptably high levels of false positive results which cause healthly individuals to suffer distress.

It then became apparent that a tendency of the prior art was the identification of shorter epitopes. This is because of the ease and lower cost with which they could be prepared and more importantly because of the reduced risk of obtaining falsely positive test results due to the presence of shared epitopes with viral proteins not related to AIDS. In this regard, Gallaher, (Cell 50, 327–328, 1987) has found that a region of the gp41 of HIV-1 shares a sequence of five adjacent amino acid residues with the respiratory syncytial virus and of four equally distributed amino acids of the measles virus F1 glycoprotein. Thus, even highly purified recombinant polypeptides containing this region, or any other common regions yet to be discovered, would potentially be responsible for falsely positive results.

Apart from its superior specificity, the identification of shorter peptide sequences corresponding to unique and highly conserved epitopes of the HIV viruses makes its production by chemical synthesis easier and cheaper. Empirical methods have been described. These methods are capable of assisting in the selection of short amino acid sequences which are likely to be exposed on the surface of the native protein (for a review see Hopp and Woods, J. Immunol. Met. 88: 1–18, 1986). Although somewhat useful, these methods are no more than indicative. Nonetheless they have been applied by many for the identification of epitopes present on the protein of the viruses responsible for AIDS. For example: U.S. Pat. No. 4,629,783, International Patent Appl. No. PCT/US86/00831. and E.P. Appl. No. 86303224 disclose various synthetic peptides from the p18, p25, gp41 and gp120 proteins of HIV-1 that are claimed useful in AIDS diagnostic kits.

This trend towards smaller antigens however is accompanied by a risk that the synthesized epitope is not able to assume a rigid conformation that is recognized by the antibody. Although the number of serum samples tested in each of these cases is very limited, specificity was found to be very high (95%–100%) with small synthetic peptides but the overall sensitivity varied between 80 and 100%. In the only example where 100% sensitivity was attained only ten samples had been tested.

Smith et al., (J. Clin. Microbiol. 25, 1498–1504, 1987) described two overlapping peptides, E32 and E34, that are highly immunoreactive. No false positive result, out of 240 seronegative specimens, were obtained but the test missed three seropositive samples out of 322 (sensitivity of 99.1%). Wang et al. (Proc. Natl. Acad. Sci. 83, 6159–6163, 1986) described a series of overlapping peptides (including amino acid residues of the E32 and E34 peptides discovered by Smith et al.) among which one 21-mer peptide showed 100% specificity and 98% sensitivity (out of 228 seropositive samples taken from patients with AIDS, 224 were found positive with this peptide).

In U.S. patent appl. Ser. No. 120,027 Filed Nov. 13, 1987, there is disclosed a short synthetic peptide covering residues 606 to 620 (SGKLICTTAVPWNAS) of gp41 (HIV-1) which is said to be immunoreactive with antibodies of patients infected by the AIDS viruses. In this example, specificity was also excellent (63/63) but 6 seropositive specimens out of 57 confirmed positive could not be detected (sensitivity of 89%).

Gnann et al. (J. Virol. 61, 2639–2641, 1987 and J. Infec. Dis. 156, 261–267, 1987) also reported a series of overlapping peptides from an immunodominant region of gp41 (HIV-1). Of particular interest was their finding that one peptide having the sequence SGKLIC (606–611) was not immunoreactive with any of the 22 HIV-1 positive sera tested. The addition of a cysteine residue to the N-terminus restored some immunoreactivity, 21 of 44 sera reacted with the 7-mer peptide (48% sensitivity). Gnann et al. concluded that cys-605 was essential for the immunoreactivity of that segment of the gp41-(HIV-1) protein.

Gnann et al. have also speculated that the cysteine residues at positions 605 and 611 (Ratner's numbering system) of gp41 (HIV-1) might play a critical role in the antigenic conformation of this region of the protein possibly through the formation of a loop via disulfide bonding. However, attempts by the authors to identify and prove the formation of the disulfide bonding have failed. Since Gnann et al. never demonstrated that they did have a synthetic peptide containing the partial amino acid sequence 605–611 wherein the two terminal cysteine groups were linked by disulfide bonds, the properties of a peptide having such a disulfide bond are unknown and unpredictable.

The 7-amino acid partial sequence containing two cysteine residues at position 605–611 also has been disclosed in other documents such as PCT/US 86/00831 published on Nov. 6, 1986 under International Publication No. WO 86/06414 where peptide X(39), which is encoded by the region from about bp 7516 through 7593, and peptide XIII(79) which is encoded by the region extending from about bp 7543 through bp 7593, both contain the 7-amino acid sequence (amino acids 605–611) discussed by Gnann et al. in the above noted publication. The peptides are reported as linear and the authors have not mentioned any formation of cyclic structures.

Rosen et al. in PCT/US 87/00577 published on Oct. 8, 1987 under International Publication No. WO 87/06005 have reported that a series of synthetic peptides encompassing the Cys(605)–Cys(611) residues of the HIV-1 envelope glycoprotein (gp41) undergo a series of spontaneous oxidative transformations upon solubilization in neutral or basic aqueous buffer. The authors have speculated that under these conditions, the peptides used in ELISAs are a random mixture of linear monomer, cyclic monomer, linear or cyclic dimers and linear polymers of various lengths. However, the inventors did not prove the presence of cyclic components and have not characterized the other various dimers and polymers present, they have speculated that the polymer forms are the most important components for reactivity in ELISA testing.

Gnann et al. (Science 237, 1346–1349, 1987) reported a short linear synthetic peptide covering residues 592 to 603 of gp42 (HIV-2) that contains two cysteines in a region homologous to the one on gp41 (HIV-1) including Cys(605) and Cys(611). This peptide reacted with 5 out of 5 sera taken from HV-2 infected patients.

Although the references discussed above do provide peptides which are useful in identifying HIV-1 antibodies, they also present certain drawbacks such as inability to full detection (100%) of positive serum samples. For example, Gnann et al. (J. Virol. 61, 2639–2641, (1987)) in their tests with their 600–611 amino acid sequence detected 22 out of 22 positive sera however they also stated that similar tests carried out by another author at the Centers for Disease Control, Atlanta, Ga. with the same 12-amino add sequence (600–611) detected 78 out of 79 positive sera. Gnann et al. in J. Infect. Dis., 156, 261–267, 1987 showed that the same 12-amino acid sequence from gp41-(HIV-1) was shown to be reactive with 131 out of 132 HIV-1 infected patients from the United States.

In the same article, it is also clearly shown that when the HIV-1 positive sera are diluted by a factor exceeding 500, some of these diluted sera are found to be negative thus indicating a low sensitivity.

Another potential drawback of these prior art assays is their use of a poorly defined and unpredictable peptide mixture as the probe. This mixture comprises peptides having many oxidative forms of cysteine produced spontaneously during peptide preparation, processing and use.

It would appear highly desirable to provide peptides or peptide mixtures which are resistant to spontaneous oxidation. Such peptides would, thus, have a well defined structure. Moreover, such peptides would, under normal test conditions, detect all HIV-1 and/or HIV-2 antibody-containing samples as positive even when extremely low levels of antibody are present.

SUMMARY OF THE INVENTION

In accordance with the present invention, there is now provided a novel series of peptides or amino acid sequences which are particularly adapted in detecting 100% of HIV-1 and HIV-2 antibodies and which are still capable of fully detecting all the HIV-1 and HIV-2 antibodies even when the sera are highly diluted.

More specifically, the novel peptides of the present invention comprise any amino acid sequence extending from 586 to 629 (gp41-HIV-1) wherein in any selected amino acid sequence there is always present the amino acid sequence which contains the cysteine residues at each terminus of the 605–611 amino acid sequence which are linked by a disulfide bond to provide the following partial sequence

-CSGKLIC-
605   611

Still more specifically, the novel cyclic peptides of the present invention are depicted in formula I and comprise therein the amino acid sequence 605–611 (gp41-HIV-1):

(I)

a-x-CSGKLIC-y-b wherein x represents if present one to nineteen amino acids corresponding to $AA_{604}$ to $AA_{586}$–$AA_{604}$ of gp41 (HIV-1) or analogues thereof; y if present represents one to eighteen amino acids corresponding to $AA_{612}$ to $AA_{612}$–$AA_{624}$ of gp41 (HIV-1) or analogues thereof; a represents the amino terminus or a substituent effective as a coupling agent and/or to make the peptide more useful as an immunodiagnostic reagent without changing its antigenic properties; and b represents the carboxy terminus or a substituent effective as a coupling agent and/or to make the peptide more useful as an immunodiagnostic reagent without changing its antigenic properties.

More specifically, x may represent one of the following amino acid sequences extending from 586–604 (gp41-HIV-1)

G
WG
IWG
GIWG
LGIWG
LLGIWG
QLLGIWG
QQLLGIWG
DQQLLGIWG
KDQQLLGIWG
LKDQQLLGIWG
YLKDQQLLGIWG
RYLKDQQLLGIWG

ERYLKDQQLLGIWG
VERYLKDQQLLGIWG
AVERYLKDQQLLGIWG
LAVERYLKDQQLLGIWG
ILAVERYLKDQQLLGIWG
RILAVERYLKDQQLLGIWG and x may represent one or more of the following amino acid sequences extending from 612–629 (gp41-HIV-1):

T
TT
TTA
TTAV
TTAVP
TTAVPW
TTAVPWN
TTAVPWNA
TTAVPWNAS
TTAVPWNASW
TTAVPWNASWS
TTAVPWNASWSN
TTAVPWNASWSNK
TTAVPWNASWSNKS
TTAVPWNASWSNKSL
TTAVPWNASWSNKSLE
TTAVPWNASWSNKSLEQ
TTAVPWNASWSNKSLEQI

Also within the scope of the present invention is a combination or mixture of synthetic peptides comprising at least one peptide of the formula I (I)

a-x-CSGKLIC-y-b wherein x, y, a and b are as previously defined, in association with

- a peptide of gp120 characterized by an amino acid sequence extending from 497 to 518 (gp120-HIV-1), or
- a peptide of gp120 characterized by an amino acid sequence extending from 497 to 518 (gp120-HIV-1), a peptide of p24 characterized by an amino acid sequence extending from 241 to 263 (p24-HIV-1), and a peptide of gp41 extending from 586 to 620 (gp41-HIV-1), or
- a peptide of gp120 characterized by an amino acid sequence extending from 497 to 518 (gp120-HIV-1), and a peptide of gp41 extending from 586 to 620 (gp41-HIV-1).

In accordance with the present invention, there is thus also provided a novel series of peptides or amino acid sequences which are useful in identifying 100% of sera taken from a small number of patients infected with HIV-2. It is thus possible to use some of the peptides or mixtures of peptides described in this invention for detecting both HIV-1 and/or HIV-2.

More specifically, the novel peptides of the present invention comprise any amino acid sequence extending from 578 to 613 (of the putative gp41.7 which will be referred to as gp42-HIV-2) wherein in any selected amino acid sequence there is always present the amino acid sequence which contains the cysteine residues at each terminus of the 597–603 (gp42-HIV-2) amino acid sequence which are linked by a disulfide bond to provide the following partial sequence

-CAFRQVC-
597 603

Still more specifically, the novel cyclic peptides of the present invention comprise therein amino acid sequence 597–603 (gp42-HIV-2) of the formula II (II)

a-$x^1$-CAFRQVC-$y^1$-b wherein $x^1$ represents if present one to nineteen amino acids corresponding to $AA_{596}$ to $AA_{578}$–$AA_{596}$ of gp42 (HIV-2) or analogues thereof; $y^1$ if present represents one to eighteen amino acids corresponding to $AA_{604}$ to $AA_{604}$–$AA_{613}$ of gp42 (HIV-2) or analogues thereof; a and b are as previously defined.

More specifically, $x^1$ represents one of the following amino acid sequences extending from 578–596 of the gp42-HIV-2:

G
WG
SWG
NSWG
LNSWG
RLNSWG
ARLNSWG
QARLNSWG
DQARLNSWG
QDQARLNSWG
LQDQARLNSWG
YLQDQARLNSWG
KYLQDQARLNSWG
EKYLQDQARLNSWG
IEKYLQDQARLNSWG
AIEKYLQDQARLNSWG
TAIEKYLQDQARLNSWG
VTAIEKYLQDQARLNSWG
RVTAIEKYLQDQARLNSWG and $y^1$ represents one of the following amino acid sequences extending from 604–613 of the gp42-HIV-2:

H
HT
HTT
HTTV
HTTVP
HTTVPW
HTTVPWV
HTTVPWVN
HTTVPWVND
HTTVPWVNDS

Also within the scope of the present invention is a combination or mixture of synthetic peptides comprising at least one cyclic peptide of the formula II (II)

wherein $x^1$, $y^1$, a and b are as previously defined, in association with a peptide called peptide 203, of the external envelope glycoprotein (EGP) and characterized by an amino acid sequence extending from 486 to 508, or a peptide called peptide 204, of the EGP characterized by an amino acid sequence extending from 486 to 501.

Furthermore, it is within the scope of the present invention to use combinations of synthetic peptides comprising at least one peptide of formula I and one peptide of formula II wherein x, y, $x^1$, $y^1$, a and b are as previously defined, in the absence or in association with one or more linear peptides of the gp120 and/or p24 and/or EGP amino acid sequences previously defined.

One unexpected advantage of the novel mixtures of the present invention is that they are capable of providing complete detection of HIV antibodies derived from a large panel of sera composed of 1378 HIV-1 positive and of 5 HIV-2 positive subjects. Another advantage is the high level of specificity retained by the mixtures of the present invention resulting in a minimal number of false positives.

DETAILED DESCRIPTION OF THE INVENTION

Selection of Peptides for Synthesis

Peptides were selected for synthesis on the basis of the known amino acid sequences of the HIV-1 isolates as well as a knowledge of which regions are conserved. More recently, it has been shown that HIV-2, a recently emerging new virus, shares considerable homology with HIV-1. It is thus possible to use some of the peptides or mixtures of peptides described in this invention for detecting both HIV-1 and/or HIV-2.

In addition to known amino acid sequences, potential epitopes were chosen by using various physicochemical principles that aid in predicting which portions of the polypeptide are most likely to be surface oriented and therefore immunogenic. These include the hydrophilicity plots of Hopp and Woods (Proc. Nat. Acad. Sci. 78, 3824–3828, 1981), and a similar approach by Kyte and Doolittle (J. Mol. Biol. 157, 105–132, 1982). Also, the empirical prediction of protein conformation (Chou and Fasman, Ann. Rev. Biochem., 47, 251–276, 1978) is a useful guide in predicting which parts of the polypeptide are likely to be immunogenic. Although these theoretical approaches are useful guides, there are many exceptions including some that were discovered during the course of the present studies.

In many instances, it is desirable to modify naturally occuring sequences in order to make the peptide more useful as an immunodiagnostic reagent without changing its antigenic properties. Such changes include:

addition of a cysteine residue at the amino or carboxyl terminus in order to facilitate coupling of the peptide to a carrier protein with heterobifunctional cross-linking reagents such as sulfosuccinimidyl-4-(p-maleimidophenyl) butyrate, a preferred reagent for effecting such linkages;

addition of certain amino acids at the COOH or $NH_2$ terminus of an oligopeptide to facilitate linking of peptides to each other, for coupling to a support or larger peptide or for modifying the physical or chemical properties of the peptide. Such changes are effected by additions of tyrosine, glutamic acid or aspartic acid which can be used as linkers via an esterification reaction and lysine which can be connected by Schiff base or amide formation;

derivatization by terminal-$NH_2$ acylation, thioglycolic acid amidation, terminal-COOH amidation, e.g. ammonia, methylamine. These modifications result in changes in net charge on the peptide and can also facilitate covalent linking of the peptide to a solid support, a carrier or another peptide. These modifications are not likely to result in changes in immunoreactivity of the peptide;

methionine, an amino acid which is prone to spontaneous oxidation, can usually be replaced by norleucine without changing antigenicity.

Peptide sequences may be subject to various changes such as insertions, deletions and substitutions, either conservative or nonconservative where such changes might provide for certain advantages in their use. These changes include combinations such as gly, ala; val, ile, leu; asp, glu; asn, gln; ser, thr; lys, arg; phe, tyr; ala, ser; ala, thr; ala, val; ala, pro; ala, glu; leu, gln; gly, phe; ile, ser; and ile, met.

It may be convenient to add a "tail" consisting of a small number (1–10) of hydrophobic amino acids to facilitate passive adsorption of a peptide to a solid support. This modification can be made at either the COOH or $NH_2$ termini. The preferred addition is phe-ala-phe-ala-phe.

In accordance with the present invention, the selected cyclic peptides useful for the detection of HIV-1 antibodies are those which comprise an amino acid sequence extending from 586 to 629 gp41-(HIV-1) wherein in any selected amino acid sequence there is always present the amino acid sequence wherein the cysteine residues at each terminus of the 605–611 gp41-(HIV-1) amino acid sequence are linked by a disulfide bond to provide the cyclic peptides of formula I. The preferred cyclic peptides are those wherein:

a-x is $NH_2G$ and y-b is TTAVPWNAS-COOH (80)

a-x is $NH_2$-RILAVERYLKDQQLLGIWG- and y-b is -TTAVPWNAS-COOH (87c)

a-x is $NH_2$-VERYLKDQQLLGIWG- and y-b is -TTAVPWNAS-COOH (88) and a-x is $NH_2G$ and y-b is -TTAVPWNASWSNKSLEQI-COOH (96)

Also in accordance with the present invention, the selected cyclic peptides useful for the detection of HIV-2 antibodies are those which comprise an amino acid sequence extending from 578 to 613 (gp42-HIV-2) wherein in any selected amino acid sequence there is always present the amino acid sequence wherein the cysteine residues at each terminus of the 597–603 (gp42-HIV-2) amino acid sequence are linked by a disulfide bond to provide the partial sequence of the formula II.

The preferred cyclic peptides of formula II in accordance with the present invention are those wherein a-$x^1$ is $NH_2$-RVTAIEKYLQDQARLNSWG- and $y^1$-b is -$CONH_2$ (peptide 146)

a-$x^1$ is $NH_2$-QDQARLNSWG- and $y^1$-b is -HTTVPWVNDS-$CONH_2$ (peptide 147)

a-$x^1$ is Ac.QDQARLNSWG- and $y^1$-b is -$CONH_2$ (peptide 200)

a-$x^1$ is $NH_2G$ and $y^1$-b is -HTTVPWVNDS-COOH (peptide 201) and a-$x^1$ is $NH_2$-RVTAIEKYLQDQARLNSWG- and $y^1$-b is HTTVPWVNDS-COOH (peptide 202).

The most preferred cyclic peptides are peptides 80, 87c, 146, 147, 200, 201 and 202.

TABLE I provides the amino acid position numbers for HIV-1 based on the sequence published by Ratner et al., Nature 313, p. 277–284, (1985) and those for HIV-2 based on the sequence published by Guyader et al, Nature 326, 662–669 (1987) for the preferred cyclic peptides of the present invention.

TABLE I

| Peptide No. | Amino acid position number on: | |
| --- | --- | --- |
| | gp41-HIV-1 | gp42-HIV-2 |
| 80 | 604–620 | |
| 87c | 586–620 | |
| 88 | 590–620 | |
| 96 | 604–629 | |
| 146 | | 578–603 |
| 147 | | 587–613 |
| 200 | | 587–603 |
| 201 | | 596–613 |
| 202 | | 578–613 |

Because regions identified are so immunoreactive both in detecting antibodies to HIV-1 and HIV-2, it is also obvious that the corresponding regions of any HIV isolates is also of interest. Similarly, sequences found on other isolates or other serotypes of HIV are also within the scope of the present invention.

Also within the scope of the present invention is the addition of one or two thiol containing residues such as cysteines to linear peptide sequences thereby providing residues for the preparation of corresponding cyclic peptides.

Generally speaking, deamino-dicarba analogs may be synthesized by the substitution of two cysteines involved in a disulfide bridge by aminosuberic acid (Asu) at position 611 of gp41-(HIV-1) or 603 of gp42-(HIV-2).

It may be desirable to covalently join two or more peptide sequences or even to form a polymer consisting of two or more peptides. Such changes may facilitate passive adsorption of the antigen to a solid surface without losing antigenic properties.

Preparation of Linear and Cyclic Peptides

The resin support is any suitable resin conventionally employed in the art for solid phase preparation of polypeptides, preferably p-benzyloxyalcohol polystyrene and p-methylbenzydrylamine resin. Following the coupling of the first protected amino acid to the resin support, the amino protecting group is removed by standard methods conventionally employed in the art of solid phase peptide synthesis. After removal of the amino protecting group, remaining α-amino protected and, if necessary, side chain protected amino acids are coupled, sequentially, in the desired order to obtain the product. Alternatively, multiple amino acid groups may be coupled using solution methodology prior to coupling with the resin-supported amino acid sequence.

The selection of an appropriate coupling reagent follows established art. For instance, suitable coupling reagents are N,N'-diisopropylcarbodiimide or N,N'-dicyclohexylcarbodiimide (DCC) either alone or preferably in the presence of 1-hydroxybenzotriazole. Another useful coupling procedure makes use of preformed symmetrical anhydrides of protected amino adds.

The necessary α-amino protecting group employed for each amino acid introduced onto the growing polypeptide chain is preferably 9-fluorenylmethyloxycarbonyl (Fmoc), although any other suitable protecting group may be employed as long as it does not suffer degradation under the coupling conditions while being readily removable selectively in the presence of any other protecting groups already present in the growing molecule.

The criteria for selecting groups for the side chain amino acids are: (a) stability of the protecting group to the various reagents under reaction conditions selective for the removal of the α-amino protecting group at each step of the synthesis: (b) the protecting group must retain its strategic properties (i.e. not be split off under coupling conditions ) and (c) the protecting group must be readily removable upon conclusion of the polypeptide synthesis and under conditions that do not otherwise affect the polypeptide structure.

The fully protected resin-supported peptides are cleaved from p-benzyloxy alcohol resin with 50 to 60 percent solution of trifluoroacetic acid in methylene chloride for 1 to 6 hours at room temperature in the presence of appropriate scavengers such as anisole, thioanisole, ethyl methyl sulfide, 1,2-ethanedithiol and related reagents. Simultaneously, most acid labile side-chain protecting groups are removed. More acid resistant protecting groups are removed by HF treatment.

Cyclic peptides of this invention are prepared by the direct oxidative conversion of protected or unprotected SH-groups to a disulfide bond by the following techniques generally known in the art of peptide synthesis. The preferred method involves the direct oxidation of free SH-groups with potassium ferricyanide. Such cyclic peptides assume a more rigid conformation which may favor binding to the antibody. It is not known whether cysteine to cysteine disulfide bonds exist in the native viral proteins.

Peptide Mixtures

Also within the scope of the present invention are mixtures of cyclic and linear peptides which have surprisingly been found to provide full detection of HIV-1 and HIV-2 antibodies derived from a large panel of sera of 1378 HIV-1 positive subjects and 5 HIV-2 positive subjects. Also it has been found that the novel mixtures of the present invention provide a high level of specificity resulting in a minimal number of false positives.

Moreover the mixtures of the present invention comprise at least one cydic peptide of the general formula

wherein x, y, a and b are as defined previously in combination with
  a linear peptide of gp120 (HIV-1), or
  a linear peptide of gp120 (HIV-1), a linear peptide of p24 (HIV-1) and a linear peptide of gp41 (HIV-1), or
  a linear peptide of gp120 HIV-1 and a linear peptide of gp41 (HIV-1).

Other mixtures of the present invention comprise at least one cyclic peptide of the general formula:

wherein $x^1$ and $y^1$ are as previously defined in combination with one of the linear peptides of the EGP of HIV-2.

Even though the cyclic peptides derived from the gp41-(HIV-1) and gp42-(HIV-2) mimic a highly conserved and immunodominant region, it was found safer to indude other peptide sequences of gp41 (HIV-1) and some from two other immunogenic proteins of HIV-1. In the event that a mutation would modify this epitope to the extent that antibodies contained in the serum of such an infected person were no longer capable of binding to the cyclic peptides, this serum could still be found positive because of the other antibodies directed against the other epitopes contained in the assay system. There is a limit though to the number of peptides that can be used in a mixture. First of all, too many different peptides might increase the rate of false positive results. In particular, many peptides of the p24 (HIV-1) protein were often found responsible for unacceptable low specificity. Secondly, the addition of too many peptides in a mixture would dilute the immunodominant one(s) and lower the sensitivity of the test.

More specifically, the linear peptide of gp120 (HIV-1) has the amino acid sequence extending from 497 to 518 and corresponds to the formula $NH_2$-CGKIEPLGVAPTKAKRRVVQREKR-COOH (71)

The linear peptide of p24 (HIV-1) has the amino acid sequence extending from 241 to 263 and corresponds to the formula $NH_2$-CGSTLQEQIGWNTNNPPIPVGEIYK-COOH (61)

The linear peptides of EGP (HIV-2) have amino acid sequences extending from 486 to 501 (peptide 204) or from 486 to 508 (peptide 203).

$NH_2$LVEITPIGFAPTKEKRYSSAHGR-COOH (203)

$NH_2$LVEITPIGFAPTKEKR-COOH (204)

HIV Antibody Detection

The peptides and the peptide mixtures of the present invention are used as diagnostic reagents for the detection of AIDS-associated antibodies in accordance with methods well-known in the art.

The main advantage of the present peptides in the determination of antibodies against AIDS resides in their specificity when compared with known antigens used so far.

According to one method for the determination of antibodies against AIDS virus, the so-called “Western Blotting” analysis is used (Towbin, H., Staehelin, Th. and Gordon, J., Proc. Nat. Acad. Sci. U.S.A. 76, 4350–4354 (1979)). According to this technique a peptide or peptides of the present invention is or are applied to nitrocellulose paper. This nitrocellulose paper is saturated and then treated with the serum to be tested. After washing, the nitrocellulose paper is treated with an anti-human IgG labeled with an enzyme. The enzymatic activity is then determined by a suitable substrate. Of course other labels like radioactive or fluorescence labels may be used.

A preferred convenient and classical technique for the determination of antibodies against AIDS virus using a peptide or a peptide mixture of the present invention is an enzyme-linked immunosorbent assay (ELISA). According to this test a peptide or a peptide mixture of the present invention is adsorbed onto the wells of a microtiter plate. The wells are then treated with sera to be tested. After washing, anti-human IgG labeled with peroxidase is added to the wells. The determination of the peroxidase is performed with a corresponding substrate, e.g. with o-phenylene diamine. Also in this procedure the peroxidase can be exchanged by another label, e.g. by a radioactive or fluorescence label.

In the ELISA test, it is possible to use individual peptides or a combination thereof. The latter is preferable since it allows one to combine the most effective peptides for detecting antibodies while at the same time excluding those that contribute to false responses. It was discovered during the course of these studies that some serum samples gave correct positive results with mixtures of peptides while giving equivocal responses with individual peptides as antigen. Thus a fully reliable test for HIV-1 and HIV-2 antibodies can only be achieved with an appropriate combination of peptide antigens.

Another method for the determination of antibodies against AIDS virus with the peptides or mixture of peptides of the invention is an enzyme immunological test according to the so-called “Double-Antigen-Sandwich-Method”. This method is based on the work of Maiolini, R. I., as described in Immunological Methods 20, 25–34 (1978). According to this method, the serum to be tested is contacted with a solid phase on which a peptide or mixture of peptides of the present invention is coated (capture layer) and with a peptide or a peptide mixture of the present invention which is labeled with peroxidase (probe layer). The immunological reaction can be performed in one or two steps. If the immunological reaction is performed in two steps, then a washing step is performed between the two incubations. After the immunological reaction or reactions, a washing step is performed. Thereafter the peroxidase is determined with a substrate, e.g. with o-phenylene diamine.

Suitable solid phases are organic and inorganic polymers [amylases, dextrans, natural or modified celluloses, polyethylene, polystyrene, polyacrylamides, agaroses, magnetite, porous glass powder, polyvinyldiene fluoride (kynar) and latex], the inner wall of test vessels (test tube, titer plates or cuvettes of glass or articifial material) as well as the surface of solid bodies (rods of glass and artificial material, rods with terminal thickening, rods with terminal lobes or lamallae). Spheres of glass and artificial material are especially suitable solid phase carriers.

The peptides and mixtures of peptides of the present invention are not only useful in the determination of antibodies against AIDS virus, but also for the determination of the AIDS virus itself since these peptides either free, polymerized or conjugated to an appropriate carrier are useful in eliciting antibodies, in particular monoclonal antibodies, against AIDS virus. Such antibodies can be produced by injecting a mammalian or avian animal with a sufficient amount of a peptide or mixture of peptides of the present invention and recovering said antibodies from the serum of said animals.

Suitable host animals for eliciting antibodies include mammals such as rabbits, horses, goats, guinea-pigs, rats, mice, cows, sheep, etc.

Various methods which are generally known can be employed in the determination of AIDS virus or a portion thereof.

In one such procedure known amounts of a serum sample to be assayed, radiolabeled cyclic peptide or mixtures of peptides of the present invention and unlabeled peptide or mixture of peptides of the present invention are mixed together and allowed to stand. The antibody/antigen complex is separated from the unbound reagents by procedures known in the art, i.e. by treatment with ammonium sulphate, polyethylene glycol, second antibody either in excess or bound to an insoluble support, dextran-coated charcoal and the like. The concentration of the labeled peptide or mixture of peptides of the present invention is determined in either the bound or unbound phase and the AIDS content of the sample can then be determined by comparing the level of labeled component observed to a standard curve in a manner known ‘per se’.

Another suitable method is the "Double-Antibody-Sandwich-Assay". According to this assay the sample to be tested is treated with two different antibodies. One of these antibodies is labeled and the other is coated on a solid phase. The suitable are solid phases are those mentioned earlier in this application. Suitable labels are enzymes, e.g. peroxidase, radio-active labels or fluorescence-labels. The preferred solid phase is a plastic bead and the preferred label is horse-radish peroxidase. Different antibodies can be raised by immunizing different animals, e.g. sheep and rabbits.

Another method consists in using the well-known Koehler and Milstein technique for producing monoclonal antibodies. In order to distinguish monoclonal antibodies which are directed against the same antigen, but against different epitopes, the method of Stähli et al. [J. of Immunological Methods 32, 297–304 (1980)] can be used.

Of course, it is also possible to use an antiserum (polyclonal antibody) and a monoclonal antibody.

According to the "Double-Antibody-Sandwich-Method", the sample is incubated with the solid phase antibody and the labeled antibody. It is possible to treat the sample first with the solid phase antibody and after washing to treat the sample with the labeled antibody. However, it is also possible to treat the sample first with the solid phase antibody and after a certain time with the labeled antibody. In addition and preferably it is possible to treat the sample together with the solid phase and the labeled antibody.

After the immunological reaction(s), there is performed a washing step. After washing the label is determined according to procedures known in the art. In the case where peroxidase is used as the label, the determination is performed with the substrate, e.g. with o-phenylene diamine or with tetramethylbenzidine. The amount of the labeled component is proportional to the amount of the antigen(s) present in the sample.

The methods for the determination of AIDS virus or of antibodies against AIDS virus as described above can be conducted in suitable test kits comprising, in a container, a cyclic peptide of the present invention or antibodies against AIDS virus elicited by a cyclic peptide or a mixture of cyclic and linear peptides of the present invention.

In addition, the cyclic peptides and mixtures of linear and cyclic peptides of the present invention can be used as a vaccine capable of inducing protective immunity against the AIDS virus. Routes of administration, antigen doses, number and frequency of injections will vary from individual to individual and may parallel those currently being used in providing immunity in other viral infections. The vaccines are prepared in accordance with known methods. The vaccine compositions will be conveniently combined with physiologically acceptable carrier materials. The vaccine compositions may contain adjuvants or any other enhancer of immune response. Furthermore, the vaccine compositions may comprise other antigens to provide immunity against other diseases in addition to AIDS.

Panel of Sera Tested

The panel of sera which were tested with the products of the present invention have been obtained from a wide variety of individuals and includes 845 samples which were known to be seronegative and 1378 samples which were confirmed seropositive for the HIV-1 and 5 samples which were confirmed seropositive for HIV-2.

TABLE 2 shows a description of the subjects from which the samples were taken as well as their HIV serological status.

TABLE 2

| | Serum status for HW-antibodies | |
|---|---|---|
| | seronegative | seropositive |
| HIV-1 Blood transfusion receivers: | | |
| thalassemia | 9 | 3 |
| kidney transplant | 21 | 1 |
| haemophiliacs | 38 | 31 |
| others | 10 | 2 |
| Viral infections: | | |
| Epstein-Barr virus | 50 | 0 |
| Cytomegalovirus | 21 | 7 |
| Papilloma | 12 | 0 |
| Hepatitis non -A, non -B | 1 | 0 |
| Lupus | 21 | 0 |
| Severe rheumatoid arthritis | 20 | 0 |
| Homosexual men | 32 | 37 |
| Unspecified | 610 | 1297 |
| HIV-2 | | |
| Unspecified | 0 | 5 |
| TOTAL | 845 | 1383 |

Results

The cyclic peptides of the present invention and their mixtures with one or more linear peptides were tested in accordance with the ELISA test described previously against a variety of sera, some of which were confirmed positive and others which were confirmed negative.

TABLE 3 provides results of single peptides which were individually evaluated in identifying known HIV-1 positive sera.

TABLE 4 provides the results of single peptides which were individually evaluated in identifying known HIV-2 positive sera.

TABLE 5 is provided to illustrate the sensitivity of cyclic versus noncyclic peptides in the ELISA test by comparing the results of some sera at various dilutions. It will be noted that within each pair, the cyclic analog is more active than its linear counterpart. These data clearly show the importance of the cyclic structure of certain peptides in reacting with the antibody.

More recently, it was found that in some conditions employed for coating (carbonate buffer, pH 9.6), linear peptides possessing two cysteines in their sequence could undergo internal cyclization and polymerization. Even though results presented in TABLE 5 clearly show the superiority of cyclic peptides over their linear counterpart in detecting HIV-1-antibodies, that increased sensitivity could have been underestimated because of probable cyclization and polymerization of the linear peptide after solubilization in a carbonate buffer (pH 9.6). That experiment was repeated with the linear 87 and cyclic 87c peptides dissolved in a carbonate buffer (pH 9.6) as before and also in 10% acetic acid (pH 2.7). HPLC analysis of the peptides confirmed that in carbonate buffer, the linear peptide 87 used underwent cyclization and polymerization when kept in solution at room temperature. It is believed that cydization and polymerization also occured in the wells of the microtiter plates although the exact proportion of cyclic peptide bound to the plates versus linear has not been as yet determined.

Contrary to what is seen in carbonate buffer, the linear peptide 87, dissolved in 10% acetic acid, remained linear as indicated by HPLC and by Ellman's test.

The cyclic peptide 87c, dissolved in 10% acetic acid, remained cyclic (from HPLC analysis and negative Ellman's test).

Plates used in this experiment were coated with solutions of peptides at 10 μg/ml. (Experimental results of TABLE 5 were obtained with plates coated with peptides at 0,5 μg/ml). Four different HIV-1 positive serum samples were serially diluted and their titers determined. The titer was defined as the serum dilution giving an absorbancy reading of 1:0 in the conditions of the ELISA procedure already described.

As already demonstrated in TABLE 5, it is still clear in TABLE 6 that cyclic peptide 87c is capable of detecting with a higher sensitivity than its linear counterpart, peptide 87, the antibodies specific to HIV-1. The ratios of sensitivities measured with the cyclic peptide over the linear 87 peptide vary between 1:3 and 2:2 with an average of 1:8. These ratios are even larger, varying from 3:0 to 4:5, when the sensitivity of the ELISA test using the cyclic 87c peptide is compared using conditions (acidic pH) where the linear 87 peptide remains linear and is not allowed to cyclize or polymerize.

Similar experiments comparing the sensitivity of plates coated with the well defined cyclic peptide 87c with others coated with a pool of chromatographic fractions containing only various polymers of peptide 87 also demonstrate the superiority of the cyclic peptide 87c in detecting HIV-1 antibodies with maximal sensitivity. In the course of these experiments it was also unexpectedly found that the background readings are significantly higher on plates coated with the linear peptide 87 (0.144±0.010 versus 0.006±0.002), and illustrates one more advantage of using the fully oxidized cyclic peptide 87c in AIDS tests.

In TABLE 7, mixtures of cyclic and linear peptides are evaluated in identifying known HIV-1 or HIV-2 positive sera and TABLE 8 shows the results of the same mixtures against HIV1 or HIV-2 negative sera.

The mixtures used in TABLE 7 and 8 are as follows.
Mixture No. Peptides in Mixture
  Linear peptides 41, 42, 56 and 71
  Linear peptides 23, 29, 42, 56 and 71
  Cyclic peptide 80 and linear peptides 61, 71 and 87
  Cyclic peptide 80 and linear peptides 71 and 87
  Cyclic peptides 80 and 87c and linear peptide 71
  Cyclic peptides 200, 201, 202 and linear peptides 203 and 204
  Cyclic peptides, 80, 87c, 202 and linear peptides 71, 203 and 204.

In these mixtures, peptides 23, 29, 203 and 204 have the following sequence $$AcNH\text{-}YGCSGKLIC\text{-}CONH_2 \quad (23)$$

$$NH_2\text{-}CGVKNWMTELL\text{-}COOH \quad (29)$$

$$NH_2\text{-}LVEITPIGFAPTKEKRYSSAHGR\text{-}COOH \quad (203)$$

$$NH_2\text{-}LVEITPIGFAPTKEKR\text{-}COOH \quad (204)$$

TABLE 9 shows a comparison of a test between mixture 4 of the present invention and the Western-Blot test in assaying 167 HIV-1 positive sera and 51 HIV-1 and HIV-2 negative sera. The results show that mixture 4 of the present invention in the ELISA test gives a higher sensitivity and specificity than the Western-Blot test.

TABLE 10 shows an immunofluorescent assay in assaying 822 HIV-1 and HIV-2 positive sera and 114 HIV negative sera. The results show that mixture 4 in the ELISA test gives higher sensitivity and specificity than the immunofluorescent assay.

TABLE 3

Efficiency of peptides in identifying HIV-1 positive sera

| Peptide No. | HIV-1 protein | % Positive Sera correctly Idenfitied | Total of positive Sera Tested |
|---|---|---|---|
| 42 | gp41 | 5 | 73 |
| 56 | gp41 | 100 | 17 |
| 77 | gp41 | 100 | 37 |
| 78 | gp41 | 100 | 37 |
| 80 | gp41 | 100 | 34 |
| 81 | gp41 | 100 | 34 |
| 87 | gp41 | 99 | 149 |
| 87c | gp41 | 99 | 114 |
| 88 | gp41 | 100 | 14 |
| 91 | gp41 | 94 | 32 |
| 95 | gp41 | 100 | 14 |
| 96 | gp41 | 100 | 14 |
| 97 | gp41 | 100 | 13 |

TABLE 3-continued

| | | | | |
|---|---|---|---|---|
| 98 | gp41 | | 100 | 14 |
| 99 | gp41 | | 100 | 15 |
| 103 | gp41 | | 100 | 13 |
| 14 | gp120 | | 50 | 10 |
| 71 | gp120 | | 83 | 186 |
| 93 | gp120 | | 37 | 29 |
| 40 | p24 | Free | 0 | 11 |
| | | coupled | 87 | 15 |
| 41 | p24 | Free | 63 | 11 |
| | | coupled | 73 | 15 |
| 46 | p24 | Free | 0 | 15 |
| | | coupled | 93 | 15 |
| 61 | p24 | Free | 100 | 3 |
| 64 | p24 | Free | 33 | 9 |

Amino acid sequence of peptides of TABLE 3

| Peptide no. | | | Amino acid number |
|---|---|---|---|
| 42 NH$_2$-TTAVPWNASWSNKSLEQGC-COOH | | gp41 | 612-628-GC |
| 56 NH$_2$-SGKLICTTAVPWNASWSNKSLEQGC-COOH | | gp41 | 606-628-GC |
| 77 NH$_2$-GCSGKLICTTAVPWNAS-COOH | | gp41 | 604-620 |
| 78 NH$_2$-IWGCSGKLICTTAVPWNAS-COOH | | gp41 | 602-620 |
| 81 NH$_2$-VERYLKDQQLLGIWGCSGKLICTTAVPWNAS-COOH | | gp41 | 590-620 |
| 87 NH$_2$-RILAVERYLKDQQLLGIWGCSGKLICTTAVPWNAS-COOH | | gp41 | 586-620 |
| 91 NH$_2$-FAFAFGCSGKLICTTAVPWNASWSNKSLEQI-COOH | | gp41 | FAFAF-604-629 |
| 95 NH$_2$-GCSGKLICTTAVPWNASWSWSNKSLEQI-COOH | | gp41 | 604-629 |
| 97 NH$_2$-CGYLKDQQLLGIWGCSGKLICTTAVPWNASWSNKSLEQI-COOH | | gp41 | CG-559-629 |
| 98 NH$_2$-CGLGIWGCSGKLICTTAVPWNASWSNKSLEQI-COOH | | gp41 | CG-600-629 |
| 99 NH$_2$-CGVERYLKQQLLGIWGCSGKLICTTAVPWNASWSNKSLEQI-COOH | | gp41 | CG-590-629 |
| 14 NH$_2$-GHACVPTDPNPQEVVL-COOH | | gp120 | 78-93 |
| 71 NH$_2$-CGKIEPLGVAPTKAKRRVVQREKR-COOH | | gp120 | GC-497-518 |
| 93 NH$_2$-TKAKRRVVQREKRGAVGIGALFLGFLGAAGSG-COOH | | gp120 | 513-535-GC |
| 41 NH$_2$-CGNNPPIPVGE-COOH | | p24 | CG-252-260 |
| 46 NH$_2$-CGRAEQASQEVKN-COOH | | p24 | CG-505-515 |
| 61 NH$_2$-CGSTLQEQIGWMTNNPPIPVGEIYK-COOH | | p24 | CG-241-263 |

TABLE 4

Efficiency of peptides in identifying HIV-2 positive sera

| Peptide No. | HIV-2 protein | % Positive sera correctly Identified | Total of positive sera tested |
|---|---|---|---|
| 146 | gp42 | 100 | 5 |
| 147 | gp42 | 100 | 5 |
| 200 | gp42 | 100 | 5 |
| 201 | gp42 | 100 | 5 |
| 202 | gp42 | 100 | 5 |
| 203 | EGP | 100 | 5 |
| 204 | EGP | 100 | 5 |

TABLE 5

Relative performance of cyclic and non-cylic peptides in ELISA (optical density units)

| Serum specimen | Dilution | 77 (linear) | vs. | 80 (cyclic) | 87 (linear) | vs. | 87c (cylic) |
|---|---|---|---|---|---|---|---|
| M-5 | 1/50 | 1.719 | | 2.104 | 1.809 | | >2.0 |
| | 1/100 | 1.459 | | 1.881 | 1.685 | | >2.0 |
| | 1/200 | 1.248 | | 1.599 | 1.513 | | >2.0 |
| | 1/400 | 0.959 | | — | 1.418 | | >2.0 |
| | 1/800 | 0.057 | | 0.767 | 1.012 | | 1.854 |
| M-7 | 1/50 | 0.142 | | 0.191 | 1.504 | | >2.0 |
| | 1/100 | 0.025 | | 0.067 | 1.329 | | >2.0 |
| | 1/200 | 0.007 | | 0.019 | 1.184 | | 1.729 |
| | 1/400 | 0.001 | | 0.010 | 0.923 | | 1.348 |
| | 1/800 | 0.000 | | 0.005 | 0.571 | | 0.611 |
| M-8 | 1/50 | 0.795 | | 1.026 | 1.390 | | >2.0 |
| | 1/100 | 0.507 | | 0.737 | 1.087 | | >2.0 |
| | 1/200 | 0.376 | | 0.520 | 0.883 | | 1.655 |
| | 1/400 | 0.209 | | 0.340 | 0.593 | | 1.064 |
| | 1/800 | 0.062 | | 0.159 | 0.240 | | 0.384 |
| M-16 | 1/50 | 1.219 | | 1.601 | 1.846 | | >2.0 |
| | 1/100 | 0.962 | | 1.300 | 1.784 | | >2.0 |
| | 1/200 | 0.613 | | 0.903 | 1.740 | | >2.0 |
| | 1/400 | 0.301 | | 0.583 | 1.634 | | >2.0 |
| | 1/800 | 0.205 | | 0.329 | 1.537 | | 1.962 |
| 87V103 | 1/50 | 0.000 | | 0.003 | 0.005 | | 0.011 |
| 1428 | 1/50 | 0.926 | | 1.047 | 1.463 | | >2.0 |

TABLE 6

Comparison of serum titers of sera measured on plates coated with a cyclic versus its linear counterpart

| Coating buffer | Serum | 87c cylic (A) | 87 linear (B) | $\frac{A}{B}$ |
|---|---|---|---|---|
| 10% Acetic Acid (pH 2.7) | M-5 | 13500 | 4500 | 3.0 |
| | M-7 | 9000 | 2300 | 3.9 |
| | M-8 | 6300 | 1400 | 4.5 |
| | M-16 | 56000 | 15000 | 3.7 |
| Carbonate Bicarbonate 0.1M (pH 9.6) | M-5 | 13500 | 10500 | 1.3 |
| | M-7 | 11000 | 6000 | 1.8 |
| | M-8 | 6500 | 2900 | 2.2 |
| | M-16 | 56000 | 33000 | 1.7 |

TABLE 7

Performance of Peptide Mixtures in Identifying HIV-1 or HIV-2 Positive Sera

| Mixture | % Positive Sera correctly Identified | Total no. of positive Sera Tested |
|---|---|---|
| 1 | 92 | 117 |
| 2 | 83 | 80 |
| 3 | 99 | 171 |
| 4 | 100 | 1378 |
| 5 | 100 | 114 |
| 6 | 100 | 5 |
| 7 | 100 | 5 |

TABLE 8

Performance of Peptide Mixtures in identifying HIV-1 or HIV-2 Negative Sera

| Mixture | % Negative Sera correctly Identified | Total no. of Negative Sera Tested |
|---|---|---|
| 1 | 100 | 14 |
| 2 | 100 | 5 |
| 3 | 95 | 21 |
| 4 | 99.4 | 845 |
| 5 | 100 | 98 |
| 6 | 100 | 10 |
| 7 | 100 | 10 |

TABLE 9

| | Mixture no. 4 of the present invention (ELISA) | Western-Blot test |
|---|---|---|
| Confirmed POS | 167 | 158 |
| False NEG | 0 | 8 |
| Confirmed NEG | 51 | 46 |
| False POS | 0 | 5 |
| Borderline | 0 | 1 |
| TOTAL TESTED | 218 | 218 |

TABLE 10

| | Mixture no. 4 of present invention (ELISA) | Immunofluorescent assay |
|---|---|---|
| Confirmed POS | 822 | 800 |
| False NEG | 0 | 1 |
| Confirmed NEG | 114 | 111 |
| False POS | 0 | 0 |
| Borderline | 0 | 24 |
| TOTAL TESTED | 936 | 936 |

The results clearly show the superiority of certain peptide mixtures, particularly the preferred ones, nos. 4 and 5, in correctly identifying known HIV-1 positive sera and of mixture 6 in correctly identifying known HIV-2 positive sera and finally mixture 7 in correctly identifying both HIV-1 and HIV-2 positive serum samples. The use of a mixture rather than a single peptide minimizes the chances of failing to identify a low titer atypical serum in which antibodies may be directed against a very limited number of epitopes. All seropositive samples were tested by ELISA and confirmed by Western Blot or immunofluorescence assay. In the event of a discrepancy, the sample was assayed by radioimmune precipitation assay which was taken as the final reference standard.

The following examples illustrate the general procedure for the synthesis and utilization of peptides of the present invention.

EXAMPLE 1

Preparation of Resins Carrying the Nα-Fmoc Protected Amino Acid Residue

The desired Nα-Fmoc protected amino acid residue in a mixture of methylene chloride ($CH_2Cl_2$) and dimethylformamide (DMF) (4:1) was added to a suspension of the p-benzyloxy alcohol resin in $CH_2Cl_2$: DMF (4:1) at 0° C. The mixture was stirred manually for a few seconds and then treated with N,N'-dicyclohexylcarbodiimide (DCC) followed by a catalytic amount of 4-(dimethylamino) pyridine. The mixture was stirred at 0° C. for an additional 30 minutes and then at room temperature overnight. The filtered resin was washed successively with $CH_2Cl_2$, DMF and isopropanol (3 washes each) and finally with $CH_2Cl_2$. The resin was suspended in $CH_2Cl_2$, chilled in an ice bath and to the stirred suspension was added redistilled pyridine followed by benzoyl chloride. Stirring was continued at 0° C. for 30 minutes and then at room temperature for 60 minutes. After filtration, the resin was washed successively with $CH_2Cl2$, DMF and isopropanol (3 washes each) and finally with petroleum ether (twice) before dried under high vacuum to a constant weight. Spectrophotometric determination of substitution according to Meienhofer et al. (Int. J. Peptide Protein Res., 13, 35, 1979) indicated the degree of substitution on the resin.

EXAMPLE 2

Coupling of Subsequent Amino Acids.

The resin carrying the Nα-Fmoc protected first amino acid residue was placed in a reaction vessel of a Labortec SP640 Peptide Synthesizer and treated as follows:

1) Wash with DMF (twice for one min. each)
2) Prewash with a 20% solution of piperidine in DMF (3 min.)
3) Deprotect with a 20% solution of piperidine in DMF (10 min.)
4) Wash with DMF (4 times 30 sec. each)
5) Wash with isopropanol (twice 30 sec. each)
6) Wash with DMF (twice 45 sec. each)
7) Check for free amino groups—Kaiser test (must be positive)
8) The peptide resin is then gently shaken for 2 min. with 3 molar equivalents of the desired F-moc-protected amino acid and 3.6 molar equivalents of 1-hydroxybenzotriazole all dissolved in dry redistilled DMF
9) Solid DCC (3.3 molar equivalents) is then added to the reaction vessel
10) Shake the reaction mixture for 2 hours
11) Wash with DMF (twice 45 sec. each)
12) Wash with isopropanol (twice for 45 sec. each)

After step 12, an aliquot is taken for a ninhydrin test. If the test is negative, one goes back to step 1 for coupling of the next amino acid. If the test is positive or slightly positive, repeat steps 6–12.

The above scheme is used for coupling of each of the amino acids of the peptides described in the invention. N-α protection with Fmoc is used with each of the remaining amino acids throughout the synthesis.

Radiolabeled peptides are obtained by the incorporation of $^3$H-glycine using the above coupling protocol.

After the addition of the last amino acid, the Nα-Fmoc of the N-terminal residue is removed by going back to steps 1–7 of the above scheme. The peptide resin is washed with $CH_2Cl_2$ and dried in vacuo to give the crude protected peptide.

EXAMPLE 3

Deprotection and Cleavage of the Peptides From the Resin

The protected peptide-resin is suspended in a 55% solution of trifluoroacetic add (TFA) in $CH_2Cl_2$ containing 2.5% ethanedithiol and 2.5% anisole. The mixture is flushed with $N_2$ and stirred for 1.5 hr. at room temperature. The mixture is filtered and the resin washed with $CH_2Cl_2$. The resin is treated again with 20% TFA in $CH_2Cl_2$ for 5 min. at room temperature. The mixture is filtered and the resin washed with 20% TFA in $CH_2Cl_2$ and then washed with $CH_2Cl_2$. The combined filtrates were evaporated in vacuo below 35° C. and the residue triturated several times with dry diethyl ether. The solid is dissolved in 10% aq. acetic acid and lyophilized to afford the crude product.

The peptides containing arg and cys residues are further deprotected by HF treatment at 0° C. for 1 hr. in the presence of anisole and dimethylsulfide. The peptides are extracted with 10% aq. acetic acid, washed with diethyl ether and lyophilized to afford the crude peptides.

EXAMPLE 4

Purification of Peptides

The crude peptides are purified by preparative HPLC on a Vydac column (2.5×25 mm) of $C_{18}$ or $C_4$ reverse phase with a gradient of the mobile phase. The effluent is monitored at 220 nm and subsequently by analytical HPLC.

Relevant fractions are pooled, evaporated and lyophilized.

The identity of the synthetic peptides is verified by analytical reverse phase chromatography and by amino acid analysis.

EXAMPLE 5

Cyclization of Peptides

A solution of potassium ferricyanide, (0.1M, pH 7.0) is added slowly to a dilute aqueous solution (0.5 mM) of the linear peptide at pH 7.0. After 2 hours at room temperature, the pH is lowered to 5.0 and the solution treated with ion exchange resin (Bio-Rad Ag-3-X4a, Cl-form) for 30 min. The suspension is filtered and the filtrate lyophilized to give the crude cyclic peptide. The peptide is purified by preparative reverse phase HPLC and characterized by amino acid analysis. Proof of a cyclic structure is obtained by comparing the HPLC mobility of the cyclic peptide with the starting linear peptide by reducing an aliquot of the cyclic peptide back to the linear peptide and also by observing the disappearance of free sulfhydryl groups (Ellman's Test) after the cydization.

In order to illustrate the physicochemical difference between cyclic peptides and their corresponding linear peptides, reference can be made to TABLE 11 which shows the difference in retention time in HPLC.

TABLE 11

| Peptide No. | Retention time in min. |
|---|---|
| 77(l) | 36.6 |
| 80(c) | 39.1 |
| 87(l) | 49.3 |
| 87c(c) | 46.1 |
| 81(l) | 49.2 |
| 88(c) | 48.7 |
| 95(l) | 48.3 |
| 96(c) | 48.5 |

(l): linear
(c): cylic

EXAMPLE 6

Conjugation of Peptides to Bovine Serum Albumin or Keyhole Limpet Hemocyanin

Peptides are conjugated to BSA or KLH previously derivatized with sulfosuccinimidyl-4-(p-maleimidophenyl) butyrate (Sulfo-SMPB).

An aqueous solution of sulfo-SMPB (Pierce Chemicals) is added to a solution of BSA or KLH in 0.02 M sodium phosphate buffer pH 7.0. The mixture is shaken at room temperature for 45 min. and the activated carrier immediately applied to a Sephadex G-25 column equilibrated with 0.1M sodium phosphate buffer pH 6.0 at 40C.

The fractions of the first peak of absorbance (280 nm), corresponding to activated carrier are combined in a round bottom flask to which is added a solution of peptide in 0.05 M sodium phosphate buffer pH 6.2. The mixture is thoroughly flushed with $N_2$ and incubated overnight at room temperature. The coupling efficiency is monitored using $^3$H-labeled peptide and by amino acid analysis of the conjugate.

EXAMPLE 7

Detection of Antibodies to HIV by an Enzyme Linked Immunosorbent Assay (ELISA)

Each well of the microtiter plate is saturated with 100 μl of a solution containing a peptide or mixture of peptides (5 μg/ml) and left overnight. The wells are emptied and washed twice with a washing buffer (Tris, 0.043M; NaCl, 0.5M;thimerosal, 0.01% w/v; Tween 20, 0.05% v/v; pH 7.4). The wells are then saturated with 0.35 ml of washing buffer for 1 hr. at 37° C. and washed once with the same buffer.

Serum samples to be analyzed are diluted with specimen buffer (washing buffer plus casein, 0.05% w/v). The wells are rinsed with washing buffer prior to the addition of the diluted serum sample (0.1 ml). These are left to incubate for 1 hr. at room temperature. The wells are then emptied, washed twice rapidly and then once for two minutes with washing buffer. The conjugate solution (affinity purified goat antibody to human IgG peroxidase labeled, 0.5 mg in 5 ml 50% glycerol) diluted with 1% w/v bovine serum albumin in washing buffer is added to each well (0.1 ml) and incubated for 1 hr. at room temperature. The wells are then emptied and washed twice rapidly with washing buffer and then five times in which the buffer was in contact with the well 2 minutes per washing.

The substrate solution (3,3', 5,5'-tetramethylbenzidine, 8 mg per ml of DMSO) is diluted with 100 volumes 0.1M citrate-acetate buffer, pH 5.6 containing 0.1% v/v of 30% $H_2O_2$ and added to each well (0.1 ml per well). After 10 minutes the contents of each well is treated with 0.1 ml 2N $H_2SO_4$ and the optical density read at 450 nm. All determinations are done in duplicate.

We claim:

1. A purified peptide having the formula

wherein:

a represents the H group which attaches to form the amino terminus or a substituent effective as a coupling agent to make the peptide more useful as an immunodiagnostic reagent without changing its antigenic properties;

b represents the OH group which attaches to form the carboxy terminus or a substituent effective as a coupling agent to make the peptide more useful as an immunodiagnostic reagent without changing its antigenic properties;

x is RVTAIEKYLQDQARLNSWG; and y is HTTVPWVNDS.

2. A method for detecting the presence of antibodies to HIV-2, said method comprising contacting an analyte suspected of containing said antibodies with the peptide of claim 1 in a manner and for a time sufficient to allow binding of said antibodies to said peptide, and detecting binding of said antibodies to said peptide.

* * * * *